Figure 1:
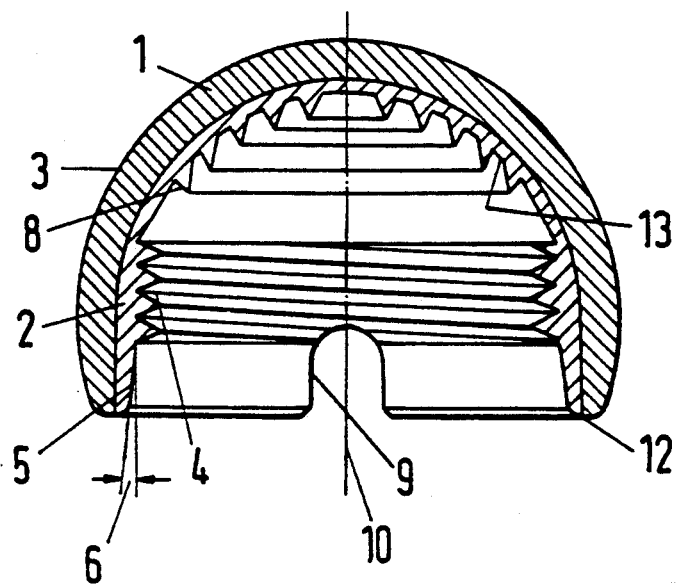

United States Patent [19]
Wagner et al.

[11] Patent Number: 5,133,769
[45] Date of Patent: Jul. 28, 1992

[54] CAP FOR A FEMUR HEAD

[75] Inventors: Heinz Wagner, Schwarzenbruck, Fed. Rep. of Germany; Roland Willi, Stadel, Switzerland

[73] Assignees: Sulzer Brothers, Winterthur; Protek AG, Berne, both of Switzerland

[21] Appl. No.: 769,182

[22] Filed: Sep. 30, 1991

[30] Foreign Application Priority Data

Nov. 9, 1990 [CH] Switzerland .............. 03567/90

[51] Int. Cl.⁵ .............................................. A61F 2/36
[52] U.S. Cl. .................................. 623/23; 623/16; 623/18
[58] Field of Search .............. 623/16, 18, 19, 21-23

[56] References Cited

U.S. PATENT DOCUMENTS

| | | | |
|---|---|---|---|
| 3,053,251 | 9/1962 | Black et al. | 623/23 X |
| 3,521,302 | 7/1970 | Muller | 623/22 X |
| 4,312,079 | 1/1982 | Dorre et al. | 623/23 |
| 4,846,841 | 6/1989 | Oh | 623/23 |

FOREIGN PATENT DOCUMENTS

| | | |
|---|---|---|
| 0017930 | 10/1080 | European Pat. Off. |
| 923383 | 8/1951 | Fed. Rep. of Germany. |
| 2751537 | 5/1979 | Fed. Rep. of Germany ........ 623/22 |
| 2225141 | 11/1974 | France. |

*Primary Examiner*—Ronald Frinks
*Attorney, Agent, or Firm*—Kenyon & Kenyon

[57] ABSTRACT

The cap for a femur head can be imbedded without the use of cement and includes an outer shell of hemispherical shape so that forces an be transferred in various positions of the joint without any discontinuity in the surface. In addition, an inner shell is secured within the outer shell and is provided with a conically tapered internal surface at the outer edge and an internal self-tapping screw thread for screwing onto a stump of a femur head. The shell also has an internal curved surface for abutting against the stump to inhibit continued threading of the cap onto the stump. Internal cutting rings may also be provided internally of the inner shell for cutting into the osseous tissue of the femur head.

6 Claims, 1 Drawing Sheet

CAP FOR A FEMUR HEAD

This invention relates to a cap for a femur head. As is known, caps for femur heads which replace a destroyed bearing surface of a hip joint are particularly suitable for relatively young patients so that the osseous tissue functions normally as far as possible. Generally, in such cases, the femur head is mechanically prepared to form as receptor stump to correspond to the internal shape cf the cap and the cap is pressed on.

U.S. Pat. Nos. 3,053,251 and 3,521,302 describe various types of caps for femur heads. However, in these cases, a primary attachment of the caps on a femur head weakens the femu neck with respect to the principal bending loads or damages the medullary space with little guarantee of a permanent attachment Other types of caps have also been known from German patent 923,383 wherein a hemispherical structure is anchored by means of a central pin or the like and from German O.S. 2751537 wherein a spherical cap is provided with a centrally exposed 18 anchor and internal thread for threading onto a femur head. Still other types of caps are described in EPA 0017 930 to adapt to a prepared surface of a femur head.

U.S. Pat. No. 4,846,841 describes a femoral prothesis which employees a cup-like insert which can be mounted over the remnant of a natural femoral head and which includes a spike for driving into the femoral head to secure the insert in place. In addition, the prothesis has a separate shell of hemispherical shape which is to be fitted over the insert.

French Patent 2,251,141 describes a cap which is provided with an internal thread for threading onto a threaded segment of a femoral head.

It is an object of the inventor to provide a primary attachment of a cap for a femur head which is effective against joint moments and which is safeguarded against tractive forces in the direction of a polar axis of the cap.

It is another object of the invention to provide a cap which can be readily imbedded without the need for bone cement on a femur head.

It is another object to the invention to be able to fix a cap on a femur head in a secure manner.

Briefly, the invention provides a cap for a femur head which is comprised of an outer shell of hemispherical shape made of a hard wearing alloy and an inner shell of hemispherical shape secured in the outer shell to bear against osseous tissue.

In addition, the inner shell has an annular edge and a conically tapered internal surface extending inwardly from the edge for engaging about a femur head. Still further, the inner shell has an internal self-tapping thread for threading onto the femur head.

The cap may be of two separate shells which are mechanically combined by a common thread or by a skrink fit. The cap may also be of one basic shell which is covered at one side with a thick plasma sprayed layer of different material and machined thereafter.

The outer shell may be made of a cobalt alloy to provide good wear characteristics while the inner shell is made of titanium to provide biocompatibility with osseous tissue.

The cap is constructed to be threaded onto a femur head via the internal self-tapping thread of the inner shell. Threading of the cap continues until the femur head abuts against the inside surface of the cap, that is, against the internal surface of the inner shell. In this way, with a primary attachment, a compression of the osseous tissue in contact with the inside of the cap occurs. Thus, the stresses acting on the cap are distributed not only as normal forces but also over a large area of the osseous tissue in the form of frictional forces.

The inner shell may also be provided with a plurality of internal concentric cutting rings for cutting into the osseous tissue of a femur head. In this respect, these rings are concentric to a polar axis of the shells.

The cap may also be provided with a plurality of circumferentially spaced recesses at least in the outer shell for engagement of a positioning tool therein.

Figure 2:
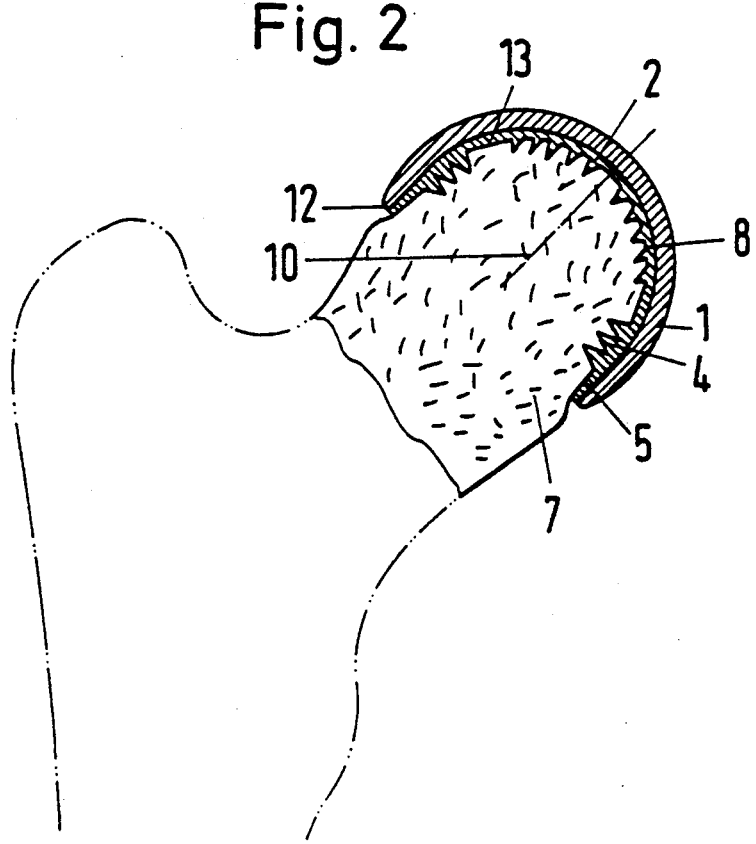

These and other objects and advantages of the invention will become more apparent from the following detailed description taken in conjunction with the accompanying drawing wherein;

FIG. 1 illustrates a cross sectional view of a cap constructed in accordance with the invention; and FIG. 2 schematically illustrates a cap in place on a femur head of a femur bone.

FIG 1, the cap 1 is constructed for mounting on a femur head without the use of cement and is in the general shape of a segment of a spherical shell. The outer surface of the cap 1 corresponds at least to a hemispherical continuous surface so that forces can be transferred in various positions of a joint without any discontinuity in the surface.

As illustrated, cap 1 is formed of an outer shell 3 of hemispherical shape made of a hard wearing cobalt alloy and an inner shell 2 of hemispherical shape secured in the outer shell 3 and made of titanium. These shells 2,3 are connected to one another so as to mutually support one another.

The outer shell 3 is made from a part of a spherical surface which is more than hemispherical and is continuous so a to provide sufficiently large transfer surfaces for the transfer of loads in different positions of the joint.

The inner shell 2 has an annular edge 12 co-planar with the annular edge of the outer shell 3 so as to form an entry into the cap 1. In addition, a conically tapered internal surface 5 extends inwardly from the edge 12, for example on a half cone angle 6 of roughly 5°. As indicated in FIG. 2, the tapered internal surface 5 is disposed for engaging about a femur head.

In addition, the inner shell 2 has an internal self-tapping thread 4 for threading onto a femur head. As indicated, the thread 4 terminates within the shell 2 at a curved surface 13 which follows the shape of the outer shell 3.

A plurality of internal concentric cutting rings 8 are also disposed inside the inner shell 2 for cutting into the osseous tissue 7 of a femur head as indicated in FIG. 2. These rings 8 are concentric to a polar axis 10 of the shells 2,3.

As shown in FIG. 1, both shells 2,3 are provided with plurality of circumferentially spaced recesses 9 for engagement of a positioning tool (not shown) therein.

In order to employ the cap 1, the stump of a femur head is prepared so as to follow the curved inner surface 13 or the inner shell 2. The external diameter of this stump is made large enough for the cap 1 to sit thereon when fixed via the tapered internal surface 5 (see FIG. 2). The cap 1 is then screwed onto the stump of the femur head by means of the positioning tool (not shown) which transmits a feed motion to the cap 1 which is guided with respect to the axis of the thread 4 and a cutting moment via the recesses 9. The feed motion for threading of the cap 1 continues until being inhibited by the impact of the curved inner surface 13 on the stump. The osseous tissue 7 under the cap 1 is thus raised or compressed at practically all contact surfaces and permits the transfer of large forces without loosening of the cap 1. The cap 1 itself is prevented from becoming loose in the direction of the thread axis by the thread 4. To this end, the thread 4 is shaped to be self-locking. This may be achieved by providing interruptions in the thread 4, for example, which become full of osseous tissue.

The cutting rings 8, when employed, enlarge the meshing surface and provide the additional absorption of parts of the transmitted joint moment. In this respect, the rings 8 protrude with a sharp edge in the direction of the thread axis, i.e., the polar axis 10, so as to become imbedded in the osseous tissue 7 as indicated in FIG. 2.

When the cap 1 is screwed on, the osseous tissue 7 touching the cap 1 and including the front surface of the femur head stump is braced or twisted when the rotational movement is inhibited by the impact of the curved inner surface 13 against the end of the stump.

The cap 1 is constructed so that the transfer of joint forces to the osseous tissue of the femur head occurs with in the spherical cap 1. The femur neck with which the largest bending moments occur on transfer to the shaft remains unaffected. The osseous tissue 7 in contact with the cap 1 is prestressed and is subject to the stimulus of the edges of the internal screwed thread 4 and cutting rings 8 for the fusion an formation of fresh osseous tissue.

For the mechanical point of view, the maximum permissible stability under load is already achieved with the primary attachment of the cap 1 to the femur head.

The invention thus provides a cap for a femur head which can be easily mounted in place without the need for bone cement and which provides a secure primary attachment.

What is claimed is:

1. A cap for a femur head comprising
   an outer shell of hemispherical shape made of a hard wearing cobalt alloy; and
   an inner shell of a hemispherical shape secured in said outer shell and made of titanium for bearing on osseous tissue, said inner shell having an annular edge, a conically tapered internal surface for extending inwardly from said edge for engaging about a femur head and an internal self-tapping thread for threading onto a femur head.

2. A cap as set forth in claim 1 wherein said inner shell includes a plurality of internal concentric cutting rings for cutting into the osseous tissue of a femur head.

3. A cap as set forth in claim 2 wherein said rings are concentric to a polar axis of said shells.

4. A cap as set forth in claim 1 wherein at least said outer shell has a plurality of circumferentially spaced recesses for engagement of a positioning tool therein.

5. A cap for a femur head comprising an outer shell of hemispherical shape made of a hard wearing alloy; and an inner shell of hemispherical shape secured in said outer shell for bearing on osseous tissue, said inner shell having an annular edge, a conically tapered internal surface for extending inwardly from said edge for engaging about a femur head and an internal self-tapping thread for threading onto a femur head.

6. A cap as set forth in claim 5 wherein said inner shell includes a plurality of internal concentric cutting rings for cutting into the osseous tissue of a femur head.

* * * * *

UNITED STATES PATENT AND TRADEMARK OFFICE
CERTIFICATE OF CORRECTION

PATENT NO. : 5,133,769
DATED : July 28, 1992
INVENTOR(S) : Sulzer Brothers Limited It is certified that error appears in the above-identified patent and that said Letters Patent is hereby corrected as shown below:

ON THE TITLE PAGE:

Abstract, line 3, change "an " to --can--

Column 1, line 10, change "cf" to --of--

1, line 36, change "inventor" to --invention--

Column 2, line 64, change "2}." to --2).--

Column 3, line 25, change "with in" to --within--

3, line 31, change "an" to --and--

Signed and Sealed this

Second Day of November, 1993

*Attest:*

BRUCE LEHMAN

*Attesting Officer*    *Commissioner of Patents and Trademarks*